US00PP21624P2

(12) United States Plant Patent
van den Top

(10) Patent No.: US PP21,624 P2
(45) Date of Patent: Jan. 11, 2011

(54) *HOSTA* PLANT NAMED 'JUSTINE'

(50) Latin Name: ***Hosta* hybrid**
Varietal Denomination: Justine

(76) Inventor: Hendrik Jan van den Top, Wesselseweg 46, 3771 PC Barneveld (NL)

( * ) Notice: Subject to any disclaimer, the term of this patent is extended or adjusted under 35 U.S.C. 154(b) by 0 days.

(21) Appl. No.: 12/590,820

(22) Filed: Nov. 14, 2009

(51) Int. Cl.
*A01H 5/00* (2006.01)

(52) U.S. Cl. ..... Plt./353
(58) Field of Classification Search ..... Plt./353
See application file for complete search history.

*Primary Examiner*—Kent L Bell
(74) *Attorney, Agent, or Firm*—C. A. Whealy

(57) ABSTRACT

A new and distinct cultivar of *Hosta* plant named 'Justine', characterized by its outwardly spreading foliage with upright flower scapes; dark green and light green variegated foliage; light violet-colored flowers that are positioned above the foliage on strong scapes; and good garden performance.

2 Drawing Sheets

Botanical designation: *Hosta* hybrid.
Cultivar denomination: 'JUSTINE'.

BACKGROUND OF THE INVENTION

The present invention relates to a new and distinct cultivar of *Hosta* plant, botanically known as *Hosta* hybrid and hereinafter referred to by the name 'Justine'.

The new *Hosta* plant is a naturally-occurring whole plant mutation of the *Hosta* hybrid 'June Fever', disclosed in U.S. Plant Pat. No. 15,340. The new *Hosta* plant was discovered and selected by the Inventor in a controlled environment in Barneveld, The Netherlands in May, 2006.

Asexual reproduction of the new *Hosta* plant by divisions in a controlled environment in Barneveld, The Netherlands since August, 2006, has shown that the unique features of this new *Hosta* plant are stable and reproduced true to type in successive generations.

SUMMARY OF THE INVENTION

Plants of the new *Hosta* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Justine'. These characteristics in combination distinguish 'Justine' as a new and distinct cultivar of *Hosta:*

1. Outwardly spreading foliage with upright flower scapes.
2. Dark green and light green variegated foliage.
3. Light violet-colored flowers that are positioned above the foliage on strong scapes.
4. Good garden performance.

Plants of the new *Hosta* differ from plants of the parent, 'June Fever', primarily in leaf coloration as leaves of plants of the new *Hosta* have a broader green-colored edge than leaves of plants of 'June Fever'. In addition, plants of the new *Hosta* have thicker leaves than plants of 'June Fever'.

Plants of the new *Hosta* can be compared to plants of 'Sweet Innocence', not patented. Plants of the new *Hosta* and 'Sweet Innocence' differ primarily in leaf coloration as plants of 'Sweet Innocence' have light green and pale yellow variegated foliage.

BRIEF DESCRIPTION OF THE PHOTOGRAPHS

The accompanying colored photographs illustrate the overall appearance of the new *Hosta* plant, showing the colors as true as it is reasonably possible to obtain in colored reproductions of this type. Colors in the photographs may differ slightly from the color values cited in the detailed botanical description which accurately describe the colors of the new *Hosta* plant.

The photograph on the first sheet comprises a side perspective view of a typical flowering plant of 'Justine' grown in a container.

The photograph on the second sheet is a close-up view of typical flowers and leaves of 'Justine'.

DETAILED BOTANICAL DESCRIPTION

The aforementioned photographs and following observations, measurements and values describe plants grown in containers in Barneveld, The Netherlands, under commercial practice during the late summer in an outdoor nursery. Plants were two years old when the photographs and description were taken. In the following description, color references are made to The Royal Horticultural Society Colour Chart, 2001 Edition, except where general terms of ordinary dictionary significance are used.

Botanical classification: *Hosta* hybrid cultivar Justine.

Parentage: Naturally-occurring whole plant mutation of the *Hosta* hybrid 'June Fever', disclosed in U.S. Plant Pat. No. 15,340.

Propagation:

*Type.*—By divisions.

*Root description.*—Medium in thickness, fibrous; creamy white in color.

*Rooting habit.*—Moderate branching; moderately dense.

Plant description:

*Plant form/habit.*—Herbaceous flowering perennial plant; mounded plant form with outwardly spreading foliage and upright flower scapes; flowering stems and leaves basal; moderately vigorous growth habit; light violet-colored flowers are positioned above the foliage on strong scapes.

*Growth rate.*—Moderately fast; about one year is required to produce fully-grown flowering plants.

*Plant height* (*soil level to top of foliar plane*).—About 15 cm to 20 cm.

*Plant height* (*soil level to top of inflorescences*).—About 45 cm.

*Plant width* (*spread*).—About 50 cm.

Foliage description:

*Arrangement/form.*—Leaves basal, simple, generally symmetrical and long-persisting.

*Leaf length.*—About 11 cm to 15 cm.

*Leaf width.*—About 5.5 cm to 9 cm.

*Shape.*—Cordate.

*Apex.*—Acuminate.

*Base.*—Rounded.

*Margin.*—Entire.

*Texture, upper and lower surfaces.*—Smooth, glabrous; leathery; moderately rugose.

*Venation pattern.*—Pinnate, arcuate.

*Color.*—Developing leaves, upper surface: Center, close to 137C; towards the margins, close to 147A. Developing leaves, lower surface: Center, close to 145B and 145C; towards the margins, close to 147A. Fully expanded leaves, upper surface: Center, more green than 146A; towards the margins, close to N137A; venation, similar to surface colors. Fully expanded leaves, lower surface: Center, close to 144A; towards the margins, close to 137B; venation, similar to surface colors.

*Petiole length.*—About 9 cm to 12 cm.

*Petiole diameter.*—About 4 mm to 8 mm.

*Petiole texture, upper and lower surfaces.*—Smooth, glabrous.

*Petiole color, upper surface.*—Close to 144A; towards the edges, close to 145D.

*Petiole color, lower surface.*—Close to 137C.

Flower description:

*Flower type/habit.*—Single campanulate flowers with fused perianth arranged on terminal racemes; flowers face mostly outwardly; panicles roughly conical in shape; freely flowering habit.

*Fragrance.*—Moderately fragrant; sweet, pleasant.

*Natural flowering season.*—Flowering recurrent during July and August in The Netherlands.

*Postproduction longevity.*—Flowers last about one week on the plant; flowers not persistent.

*Flower buds.*—Height: About 1 cm to 3 cm. Diameter: About 5 mm to 12 mm. Shape: Elliptic to obovate. Color: Close to 146D.

*Inflorescence height.*—About 14 cm to 18 cm.

*Inflorescence diameter.*—About 12 cm to 14 cm.

*Flower diameter.*—About 3 cm.

*Flower depth.*—About 5 cm.

*Perianth.*—Arrangement: Three interior tepals arranged in a single whorl surrounded by an outer whorl of three exterior tepals. Tepal length: About 1.5 cm to 2 cm. Tepal width: About 1 cm to 1.2 cm. Tepal shape: Ovate. Tepal apex: Acute. Tepal margin: Entire. Tepal texture, upper and lower surfaces: Smooth, glabrous; satiny. Tepal color: Developing and fully expanded tepals, upper surface: Close to 85B to 85C; towards the base, close to 85D. Developing and fully expanded tepals, lower surface: Close to 85D.

*Flower bracts.*—Quantity: One per flower at the base of the pedicel. Length: About 1.5 cm. Width: About 5 mm. Shape: Ovate. Apex: Acute. Base: Cuneate. Margin: Entire. Texture, upper and lower surfaces: Smooth, glabrous. Color, upper and lower surfaces: Close to 146D; towards the base, close to 193A.

*Peduncles* (*scapes*).—Length: About 22 cm to 27 cm. Diameter: About 5 mm to 6 mm. Angle: Erect. Strength: Strong. Texture: Smooth, glabrous. Color: Close to 146C.

*Pedicels.*—Length: About 9 mm to 11 mm. Diameter: About 2 mm. Strength: Strong. Texture: Smooth, glabrous. Color: Close to 146C.

*Reproductive organs.*—Stamens: Quantity per flower: Typically six; anthers dorsifixed. Filament length: About 5.5 cm. Filament color: Close to 155C. Anther shape: Narrowly oblong. Anther length: About 4 mm. Anther color: Close to 86B. Pollen amount: Moderate. Pollen color: Close to 17A. Pistils: Quantity per flower: One. Stigma shape: Lobed. Stigma color: Close to 155C. Style length: About 5 cm. Style color: Close to 145D. Ovary length: About 6 mm. Ovary color: Close to 150C.

*Seed/fruit.*—Seed and fruit development have not been observed.

Disease/pest resistance: Plants of the new *Hosta* have not been noted to be resistant to pathogens and pests common to *Hosta.*

Garden performance: Plants of the new *Hosta* have been observed to have good garden performance and to tolerate rain, wind and temperatures ranging from about −30° C. to about 35° C.

It is claimed:

1. A new and distinct *Hosta* plant named 'Justine' as illustrated and described.

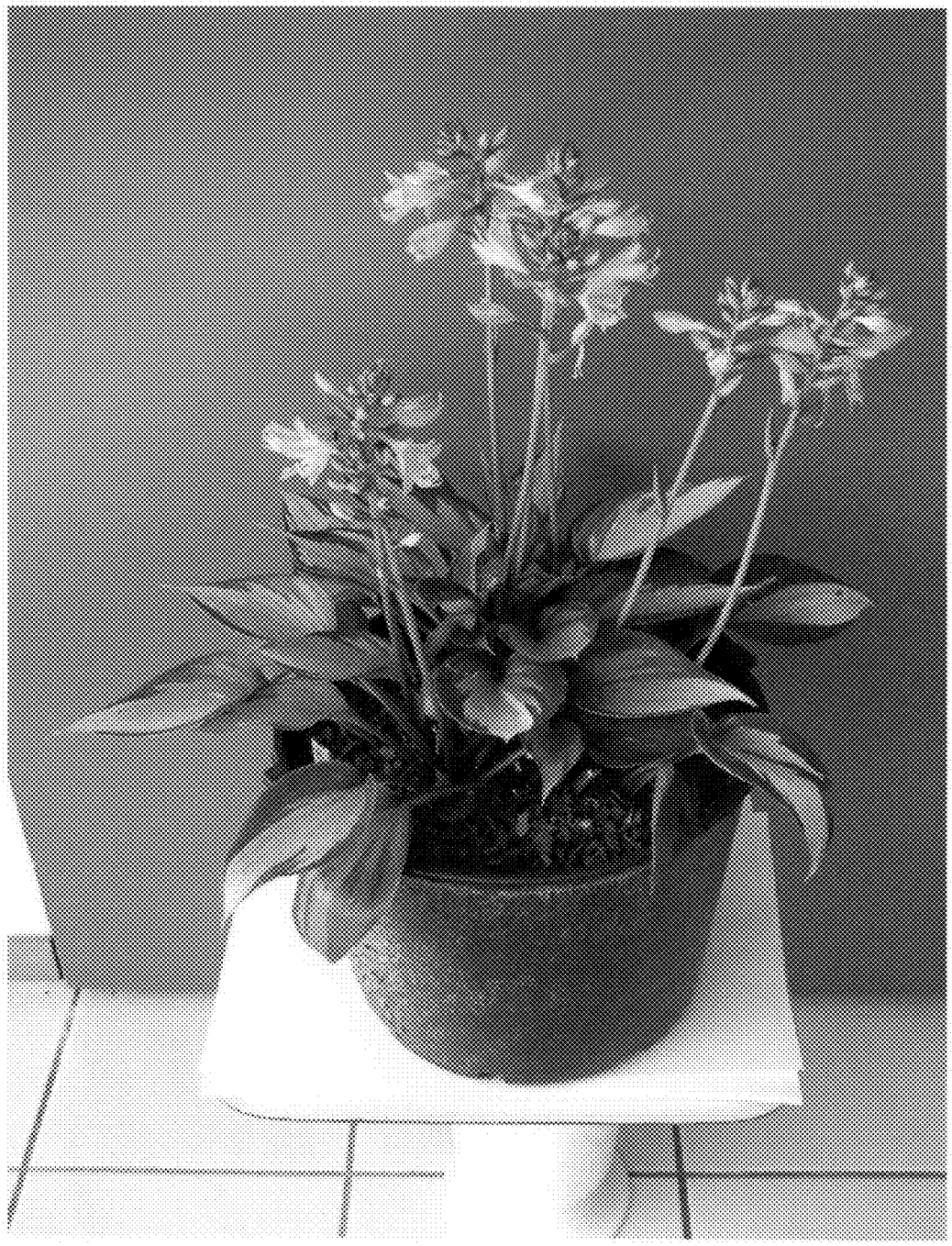

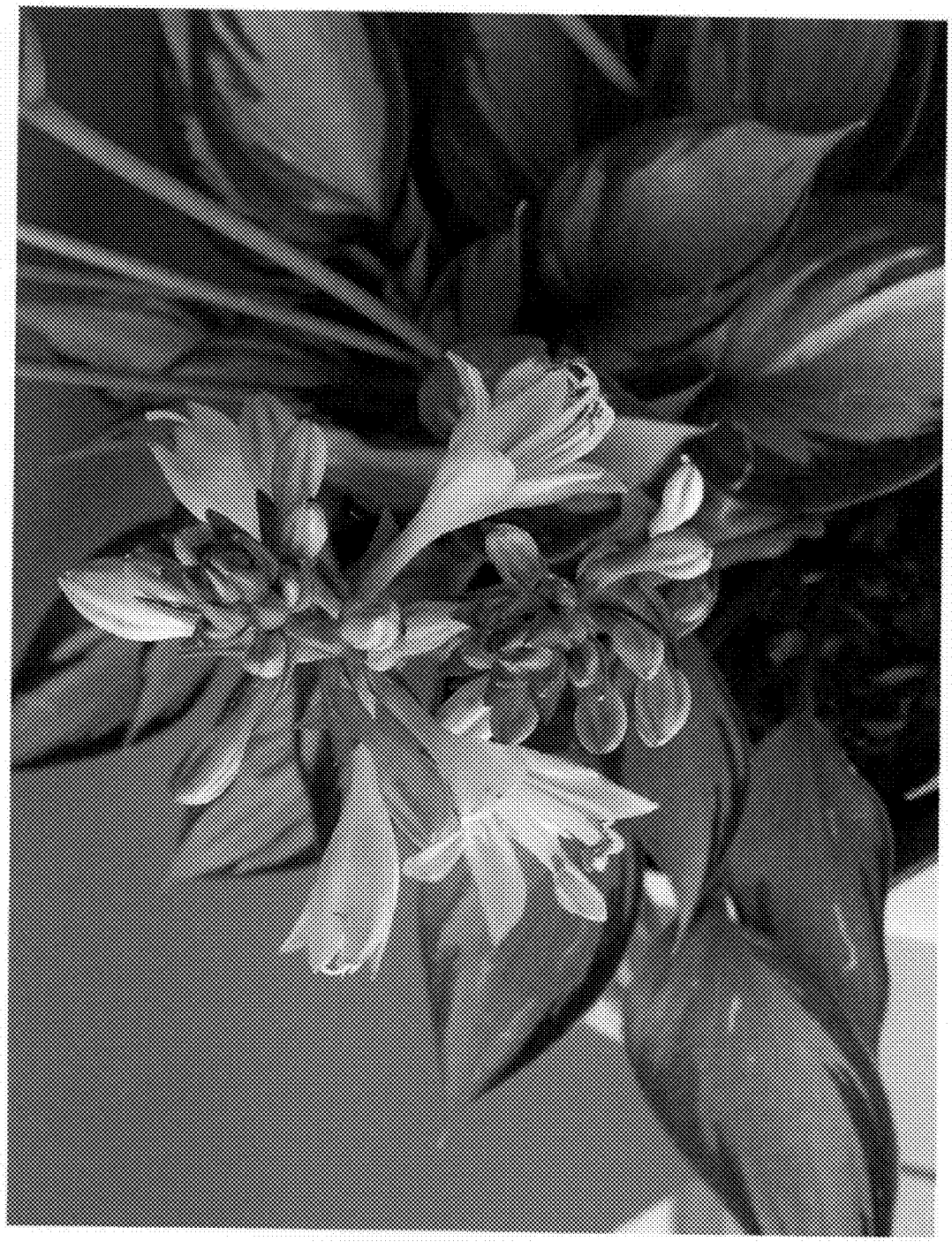

* * * * *